(12) United States Patent
Gardner, III

(10) Patent No.: US 8,378,324 B2
(45) Date of Patent: Feb. 19, 2013

(54) HANDHELD PORTABLE MULTI PURPOSE STERILIZING WAVELENGTH TRANSFORMING CONVERTER

(76) Inventor: William G. Gardner, III, Glendale, AZ (US)

( * ) Notice: Subject to any disclaimer, the term of this patent is extended or adjusted under 35 U.S.C. 154(b) by 162 days.

(21) Appl. No.: 12/854,160

(22) Filed: Aug. 10, 2010

(65) Prior Publication Data

US 2010/0320405 A1 Dec. 23, 2010

Related U.S. Application Data

(63) Continuation-in-part of application No. 12/027,270, filed on Feb. 7, 2008, now Pat. No. 7,781,751.

(51) Int. Cl.
*A61L 2/00* (2006.01)
(52) U.S. Cl. ........... 250/504 H; 250/455.11; 250/453.11
(58) Field of Classification Search ............ 250/453.11, 250/454.11, 455.11, 493.1, 494.1, 503.1, 250/504 R, 504 H; 422/22, 24
See application file for complete search history.

(56) References Cited

U.S. PATENT DOCUMENTS

| | | | | |
|---|---|---|---|---|
| 2001/0042842 A1* | 11/2001 | Leighley et al. | .......... | 250/504 H |
| 2004/0084630 A1* | 5/2004 | Waluszko | ................ | 250/455.11 |
| 2006/0261291 A1* | 11/2006 | Gardner, III | ............. | 250/504 R |
| 2007/0255266 A1* | 11/2007 | Cumbie et al. | .................... | 606/9 |
| 2008/0260601 A1* | 10/2008 | Lyon | .......................... | 422/186.3 |

* cited by examiner

*Primary Examiner* — David A Vanore
*Assistant Examiner* — Nicole Ippolito

(57) ABSTRACT

An apparatus and a method, in a handheld portable multi purpose device, for producing multiple and variable wavelength distributions of UV radiation, or visible radiation, comprising a primary UV radiation source, and a system of wavelength transforming (WT) materials that allows selecting at will between UV A, UV B, UV C radiation (individual selections or various combinations,) and visible radiation, whereby the apparatus provides for UV sterilization of food, fluid, air, fluids, and surfaces; while also providing a means to emit visible light. Additionally, an apparatus and method, in a handheld portable multi purpose device, for enabling production and emission of UV radiation selectable between UV A, UV B, UV C radiation (individual selections or various combinations,) and visible radiation in a small form factor device embodied in a handheld portable flashlight, or lamp, type device.

17 Claims, 6 Drawing Sheets

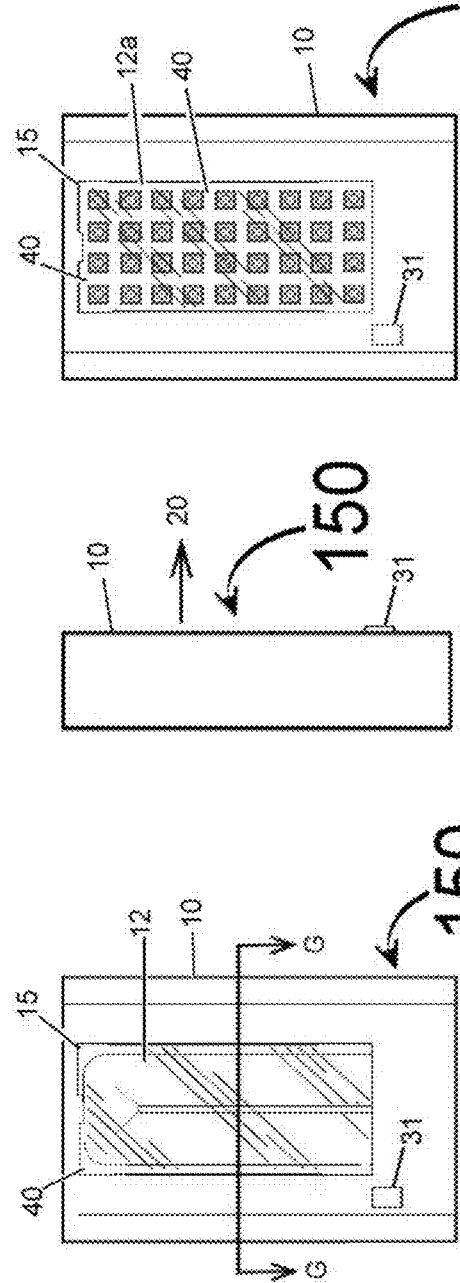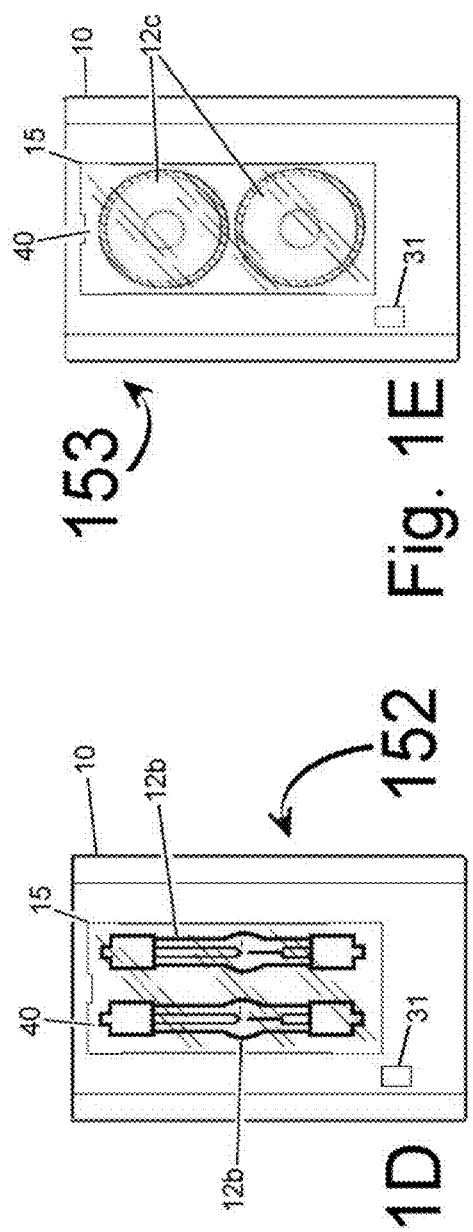

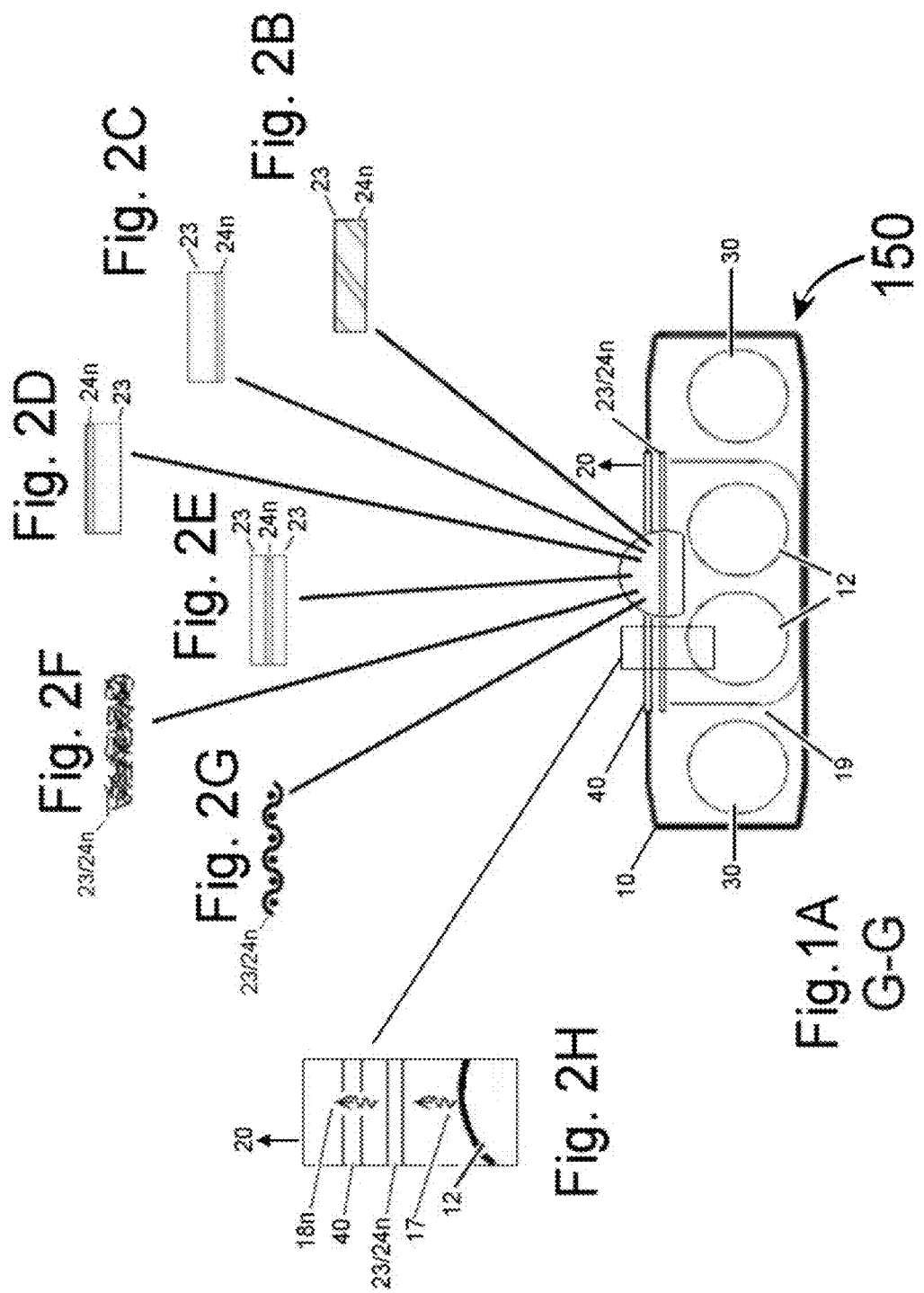

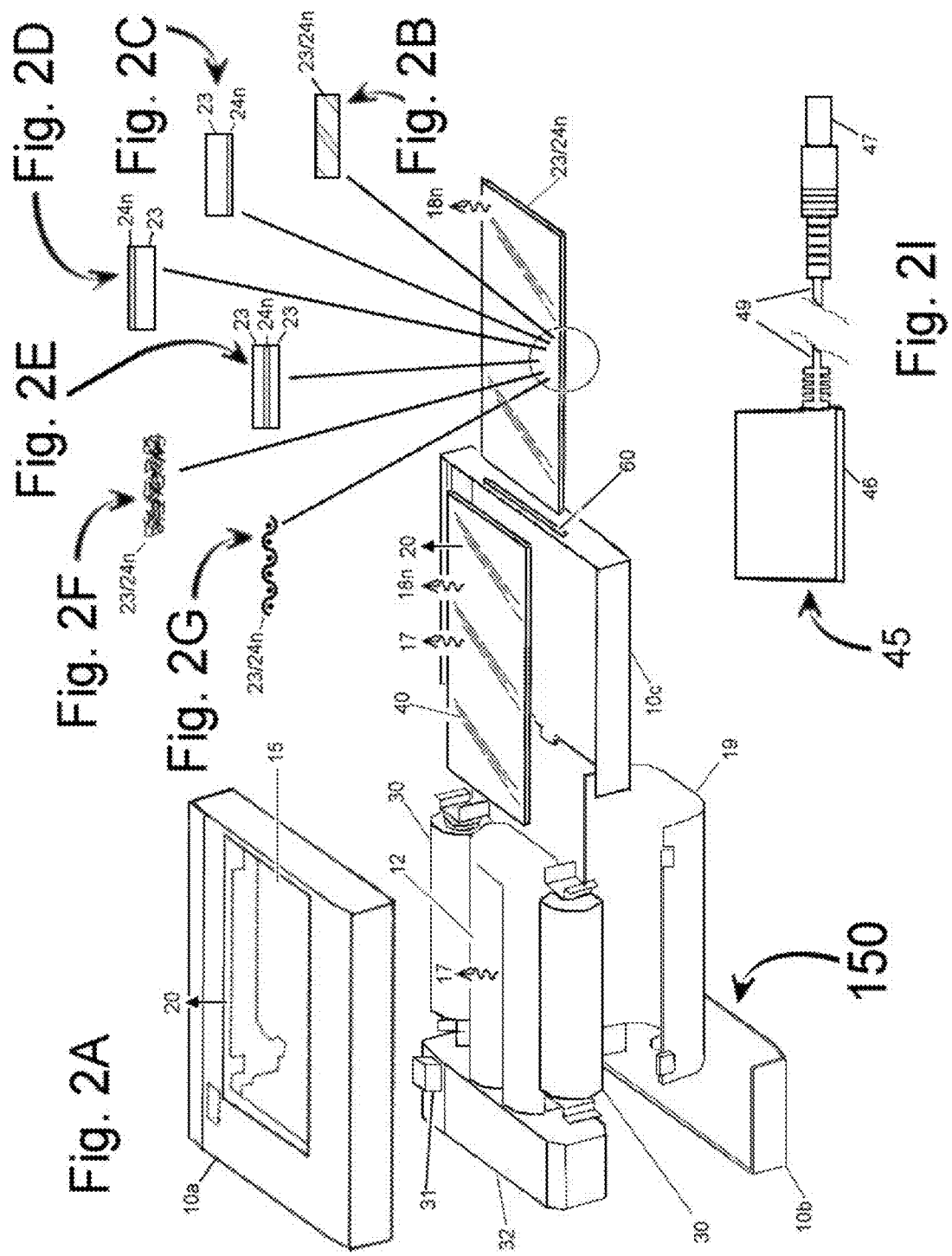

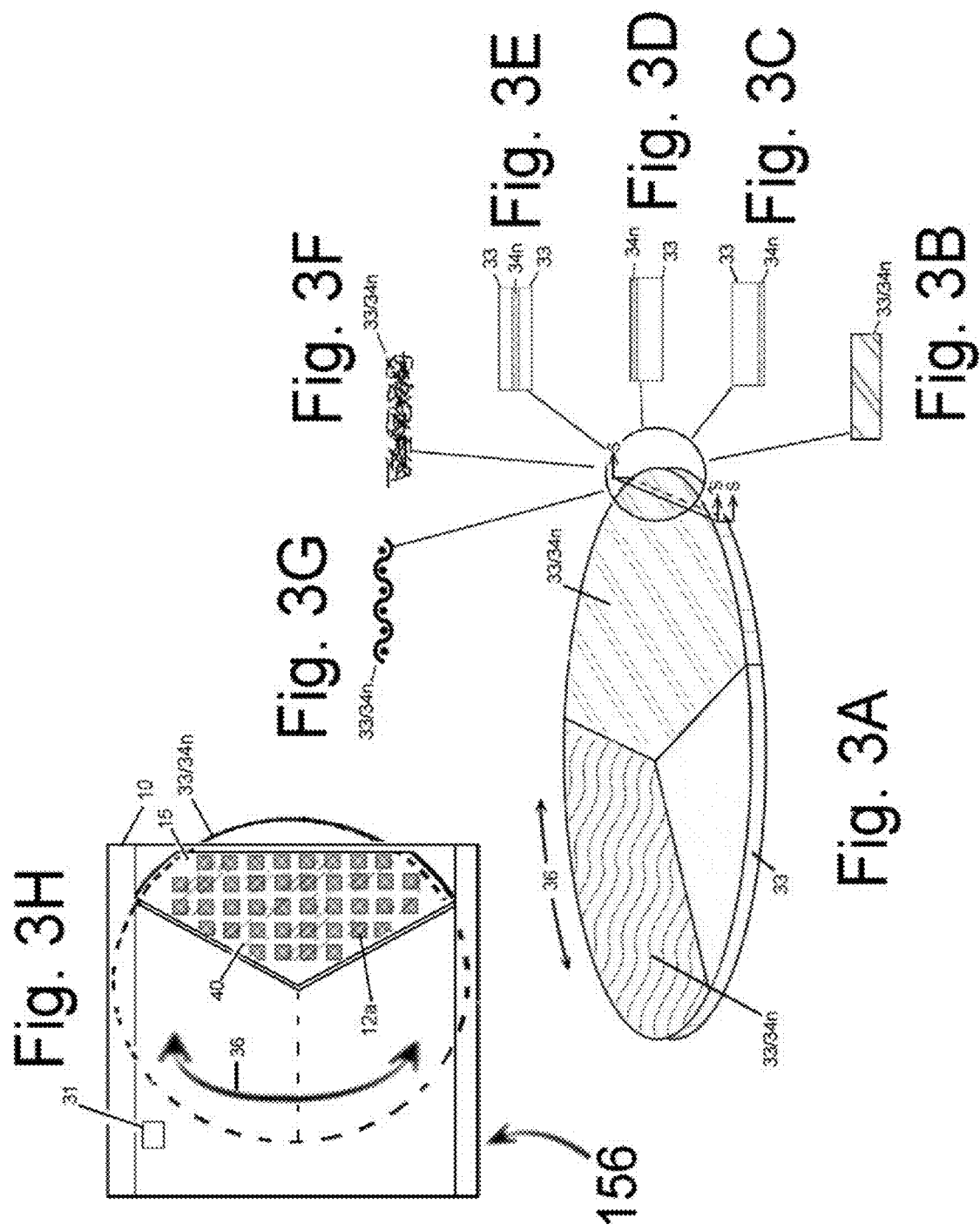

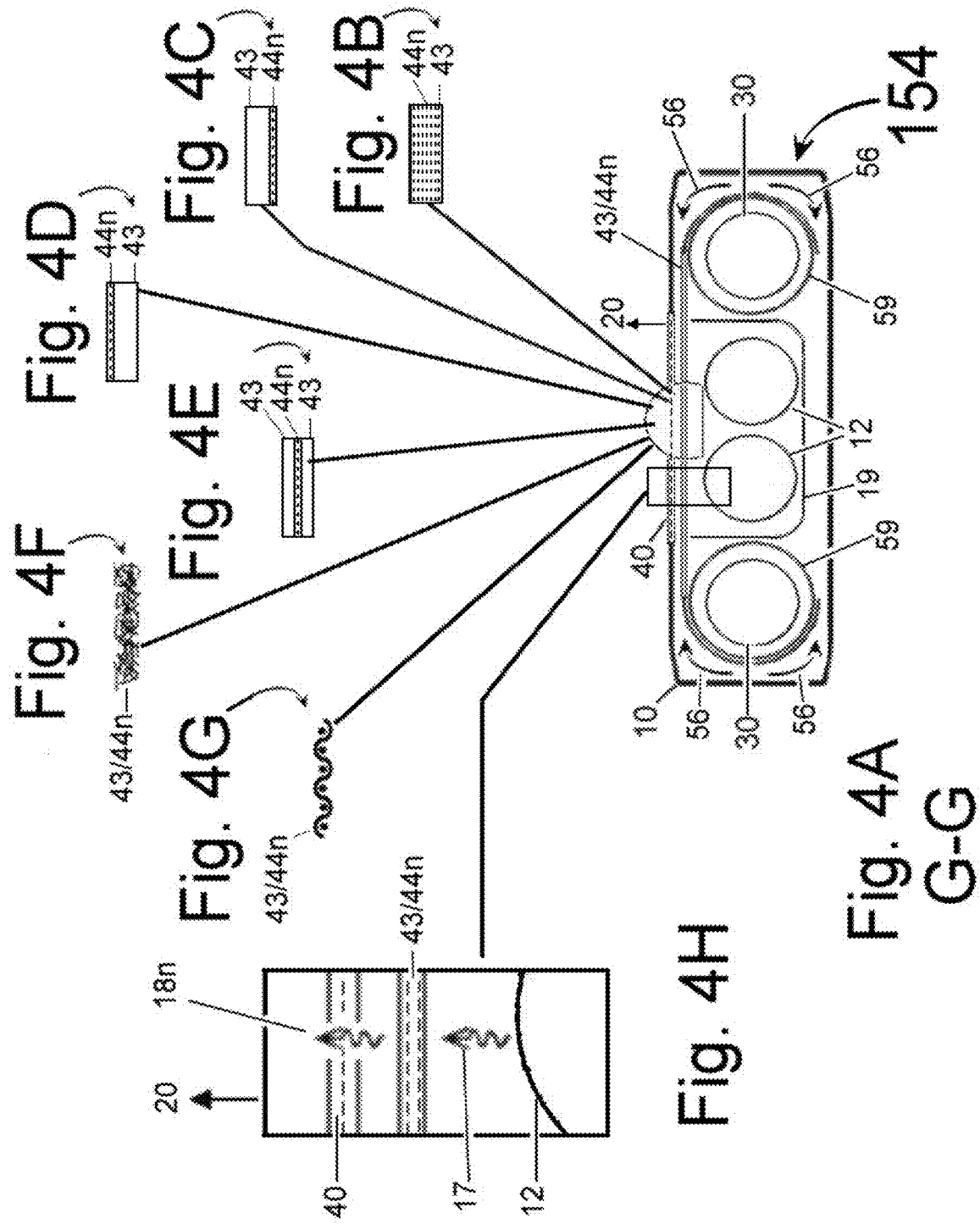

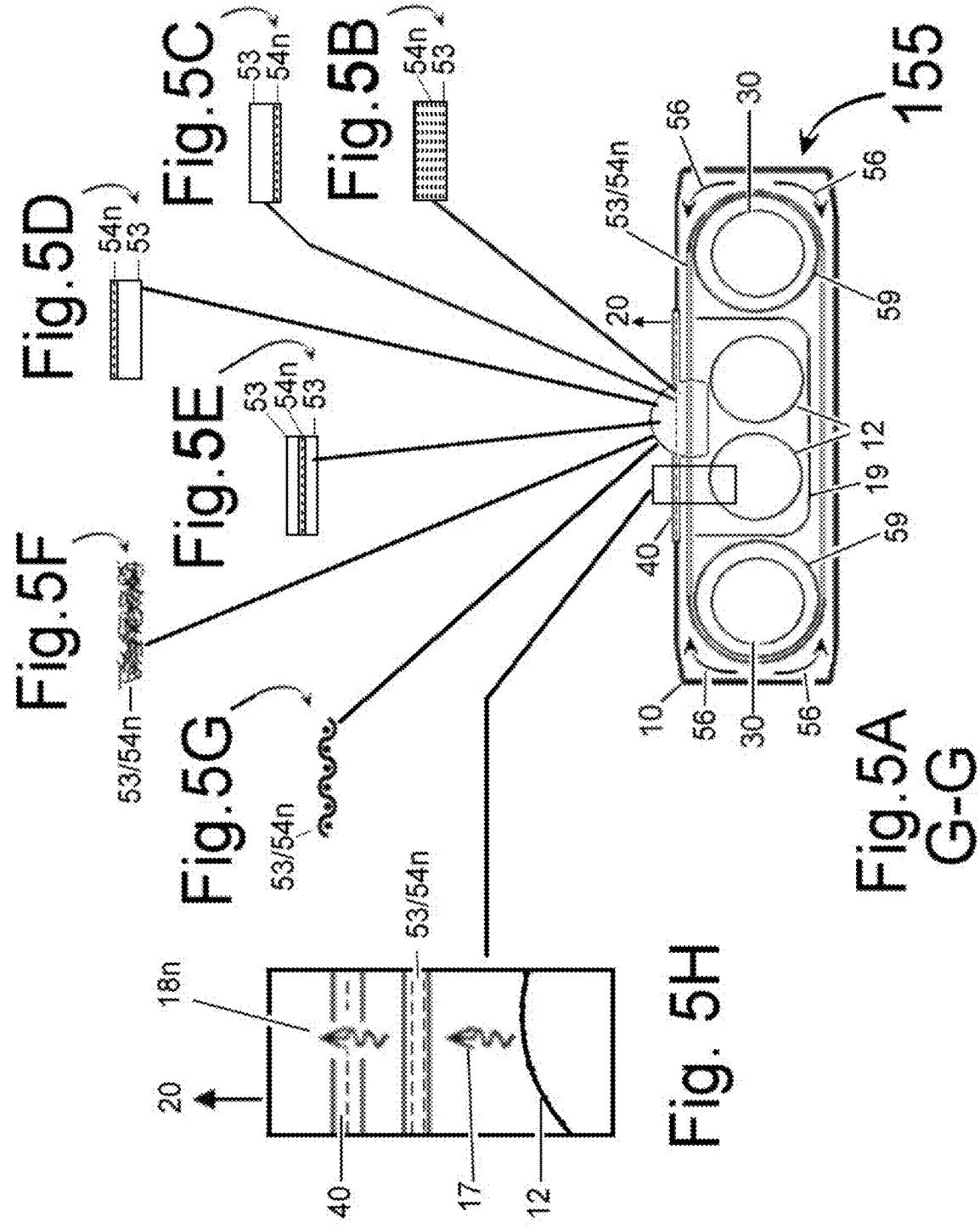

HANDHELD PORTABLE MULTI PURPOSE STERILIZING WAVELENGTH TRANSFORMING CONVERTER

CROSS-REFERENCE TO RELATED APPLICATIONS

This application is a continuation-in-part of U.S. utility application Ser. No. 12/027,270 Titled PORTABLE WAVELENGTH TRANSFORMING CONVERTER FOR UV LEDS, filed Feb. 7, 2008, now U.S. Pat. No. 7,781,751 and is incorporated by reference in its entirety herein for all purposes.

FIELD OF THE INVENTION

The present invention relates to handheld portable multi purpose ultraviolet radiation (UV) emitting devices used to provide UV sterilization of food, fluid, air, fluids, and surfaces; the fluorescing of desired minerals or materials, while also providing a means to emit visible light. Additionally, the present invention relates to handheld portable multi purpose ultraviolet radiation (UV) emitting devices used in the fields of mineralogy; scientific research; forensics; area illumination; photo-chemistry, photo-medical treatments, photo-lithography, artistic displays of fluorescent materials; and similarly related fields. Specifically, the present invention provides a system whereby the primary wavelength distribution of radiation being emitted from a primary UV radiation source may be transformed into a secondary wavelength distribution of radiation that is different from the primary wavelength distribution of radiation, while also providing the emission of radiation in the wavelength of substantially visible light.

BACKGROUND OF THE INVENTION

The electromagnetic spectrum ranges from cosmic rays at one end, to radio waves at the other end. The UV region of the electromagnetic spectrum is situated between visible light and x-rays, with the wavelengths of the UV A radiation being shorter and more energetic than violet visible light and the wavelengths of vacuum UV radiation being slightly longer and less energetic than x-rays. The full UV radiation spectrum ranges from wavelengths of about 100 nanometers (nm) to 400 nm and the UV radiation spectrum is usually divided into 4 sections; vacuum UV radiation (also called far or very UV, from 100 nm to about 200 nm), UV C radiation (also called germicide or short-wave UV, from 200 to about 280 nm), UV B radiation (also called mid-wave or medium-wave UV, from 280 nm to about 320 nm), and UV A radiation (also called "poster lamp", black-light, or long-wave UV, from 320 nm to 400 nm).

UV radiation can be emitted from a variety of sources such as light emitting diodes (LEDs), lasers, electric arcs (especially as in arc welding), xenon bulbs, halogen bulbs, excimer bulbs, eximer bulbs, and mercury vapor lamps/tubes of low, medium and high pressures. UV C radiation is used extensively for sterilization, purifying, and deodorizing applications in food, air, fluid, and general surface sterilization processes because the UV C radiation not only deactivates micro-organisms such as: bacteria, molds, spores, fungi, and viruses (by direct irradiation which damages the DNA such that the micro-organisms cannot reproduce), but the UV C radiation also breaks down the chemical bonds of alcohols, pesticides, chloramines, and other contaminants such as NDMA or MTBE. UV B radiation is the agent that causes human skin to "sun-burn" and the UV B radiation is needed to start the suntanning process. The lamps/tubes used in suntanning booths usually emit a combination of UV B and UV A. UV B is also used extensively in various medical treatments—especially for skin diseases. UV A radiation is used for special effect lighting, suntanning, photo-lithotropy, and photo-chemistry.

U.S. Pat. No. 6,787,782 teaches a system that uses UV radiation emitting LEDs as one source of UV radiation for sterilizing air in a vehicle such as an airplane. Similarly, U.S. Pat. No. 6,333,748 teaches the use of UV radiation emitting LEDs in combination with a reactive surface to sterilize air for breathing inside a helmet. Neither of these two patents teaches any way to vary or transform the radiation from the UV radiation source.

U.S. Pat. Nos. 5,736,744, 6,670,619, and 6,911,657 by Waluszko describe a wavelength-shifting filter as only emitting one particular wavelength distribution of radiation. Waluszko does not teach the use of conversion plates with LEDs.

The present invention relates to handheld portable multi purpose UV emitting devices used to provide UV sterilization of food, fluid, air, fluids, and surfaces; while also providing a means to emit visible light. Additionally, the present invention relates to handheld portable multi purpose UV emitting devices used in the fields of mineralogy; scientific research; forensics; area illumination; photo-chemistry, photo-medical treatments, photo-lithography, artistic displays of fluorescent materials; and similarly related fields. Specifically, the present invention provides a method and device whereby the primary wavelength distribution of radiation being emitted from a primary UV radiation source may be transformed into a secondary wavelength distribution of radiation that is different from the primary wavelength distribution of radiation, and wherein the device comprises a small form factor device, battery powered apparatus suited for carrying in a pocket, or by the hand, and whereby field use of the UV emitting device is very easy and

SUMMARY OF THE INVENTION

One object of the present invention is to provide an apparatus and a method, in a handheld portable multi purpose device, for producing multiple and variable wavelength distributions of UV radiation, or visible radiation, comprising a primary UV radiation source, and a system of wavelength transforming (WT) materials that allows selecting at will between UV A, UV B, UV C radiation (individual selections or various combinations,) and visible radiation, whereby the apparatus provides for UV sterilization of food, fluid, air, fluids, and surfaces; while also providing a means to emit visible light.

Another object of the present invention is to provide an apparatus and method, in a handheld portable multi purpose device, for enabling production and emission of UV radiation selectable between UV A, UV B, UV C radiation (individual selections or various combinations,) and visible radiation in a small form factor device embodied in a handheld portable flashlight, or lamp, type device.

BRIEF DESCRIPTION OF THE DRAWINGS

FIG. 1A shows a plan view of a first preferred embodiment of the invention showing apparatus 150 comprising a primary UV radiation source, low-pressure mercury vapor tube 12.

FIG. 1B shows a side view of the first embodiment of the invention, shown in FIG. 1, apparatus 150.

FIG. 1C is a plan view of a second preferred embodiment of the invention showing apparatus 151, comprising a primary UV radiation source, UV LED array 12a.

FIG. 1D is a plan view of a third preferred embodiment of the invention showing apparatus 152, comprising a primary UV radiation source, UV emitting xenon bulbs 12b.

FIG. 1E is a plan view of a fourth preferred embodiment of the invention showing apparatus 153, comprising a primary UV radiation source, UV emitting eximer/excimer bulb 12c.

FIG. 1A G-G is a cross section of the first preferred embodiment shown in FIG. 1A taken along the line G-G.

FIG. 2A is an exploded view of the first preferred embodiment of the invention shown in FIG. 1A showing apparatus 150 comprising the primary UV radiation source, low-pressure mercury vapor tube 12.

FIG. 2B is an expanded cross sectional view of a portion of a flexible WT filter 23 of apparatus 150-153, wherein a WT material 24n is uniformly distributed throughout the material comprising the WT filter 33.

FIG. 2C is an expanded cross sectional view of a portion of the flexible WT filter 23 of apparatus 150-153, showing a variation wherein the WT material 24n is coupled to the lower surface of the material comprising the WT filter 23.

FIG. 2D is an expanded cross sectional view of a portion of the flexible WT filter 23 of apparatus 150-153, showing a variation where the WT material 24n is coupled to the upper surface of the material comprising the WT filter 23.

FIG. 2E is an expanded cross sectional view of a portion of the flexible WT filter 23 of apparatus 150-153, showing a variation where the WT material 24n is laminated between two supporting upper and lower surfaces of the material comprising the WT filter 23.

FIG. 2F is an expanded cross sectional view of a portion of the flexible WT filter 12 of apparatus 150-153, showing a variation where the WT material 24n is coupled (to support uniform, lower or upper WT material and support material) to wire like shapes that form a mat comprising the material of the WT filter 23.

FIG. 2G is an expanded cross sectional view of a portion of the flexible WT filter 23 of apparatus 150-153, showing a variation where the WT material 24n is coupled with wire like shapes that form a woven mesh (similar to fiberglass cloth or metal screen) comprising the material of the WT filter 23.

FIG. 2H is an expanded cross sectional view along the line G-G of FIG. 1A of a portion of apparatus 150, comprising the primary UV radiation source 12, the flexible WT filter 23 with WT material 24n, and a lens cover 40.

FIG. 2I is a side view of an external power supply assembly capable of supplying the proper power to operate and/or charge the internal batteries of the apparatus 150-156.

FIG. 3A is an expanded perspective view of a rotatable disk shaped WT filter 33 which has multiple sections which optionally replace the single WT filter 23 shown in FIG. 1A G-G, and 2A, wherein the rotatable disk shaped WT filter 33 is coupled to a fifth preferred embodiment of the present invention, apparatus 156.

FIG. 3B is an expanded cross sectional view of a portion of a flexible WT filter 33 of apparatus 156, wherein a WT material 34n is uniformly distributed throughout the material comprising the WT filter 33.

FIG. 3C is an expanded cross sectional view of a portion of the flexible WT filter 33 of apparatus 156, showing a variation wherein the WT material 34n is coupled to the lower surface of the material comprising the WT filter 33.

FIG. 3D is an expanded cross sectional view of a portion of the flexible WT filter 33 of apparatus 156, showing a variation where the WT material 34n is coupled to the upper surface of the material comprising the WT filter 33.

FIG. 3E is an expanded cross sectional view of a portion of the flexible WT filter 33 of apparatus 156, showing a variation where the WT material 34n is laminated between two supporting upper and lower surfaces of the material comprising the WT filter 33.

FIG. 3F is an expanded cross sectional view of a portion of the flexible WT filter 33 of apparatus 156, showing a variation where the WT material 34n is coupled (to support uniform, lower or upper WT material and support material) to wire like shapes that form a mat comprising the material of the WT filter 33.

FIG. 3G is an expanded cross sectional view of a portion of the flexible WT filter 33 of apparatus 156, showing a variation where the WT material is coupled with wire like shapes that form a woven mesh (similar to fiberglass cloth or metal screen) comprising the material of the WT filter 33.

FIG. 3H shows a plan view of the fifth preferred embodiment of the invention, apparatus 156, comprising the rotatable disk shaped WT filter 33 of FIG. 3A FIG. 4A G-G is a cross section of a sixth preferred embodiment, apparatus 154, of the invention shown in FIG. 1A taken along the line G-G, wherein a WT filter 43 is in the form of a flexible belt comprising UV transmitting material that is coupled with WT materials 44n.

FIG. 4B is an expanded cross sectional view of a portion of a flexible WT filter 43 of apparatus 154, wherein a WT material 44n is uniformly distributed throughout the material comprising the WT filter 43.

FIG. 4C is an expanded cross sectional view of a portion of the flexible WT filter 43 of apparatus 154, showing a variation wherein the WT material 44n is coupled to the lower surface of the material comprising the WT filter 43.

FIG. 4D is an expanded cross sectional view of a portion of the flexible WT filter 43 of apparatus 154, showing a variation where the WT material 44n is coupled to the upper surface of the material comprising the WT filter 43.

FIG. 4E is an expanded cross sectional view of a portion of the flexible WT filter 43 of apparatus 154, showing a variation where the WT material 44n is laminated between two supporting upper and lower surfaces of the material comprising the WT filter 43.

FIG. 4F is an expanded cross sectional view of a portion of the flexible WT filter 43 of apparatus 154, showing a variation where the WT material 44n is coupled (to support uniform, lower or upper WT material and support material) to wire like shapes that form a mat comprising the material of the WT filter 43.

FIG. 4G is an expanded cross sectional view of a portion of the flexible WT filter 43 of apparatus 154, showing a variation where the WT material 44n is coupled with wire like shapes that form a woven mesh (similar to fiberglass cloth or metal screen) comprising the material of the WT filter 43.

FIG. 4H is an expanded cross sectional view along the line G-G of FIG. 4A of a portion of apparatus 154, comprising the primary UV radiation source 12, the flexible WT filter 43 with WT material 44n, and a lens cover 40.

FIG. 5A G-G is a cross section of a seventh preferred embodiment of the invention, apparatus 155, shown in FIG. 1A taken along the line G-G, wherein a WT filter 53 is in the form of a flexible continuous belt comprising UV transmitting material that is coupled with WT materials 54n.

FIG. 5B is an expanded cross sectional view of a portion of a flexible WT filter 53 of apparatus 155, wherein a WT material 54n is uniformly distributed throughout the material comprising the WT filter 53.

FIG. 5C is an expanded cross sectional view of a portion of the flexible WT filter 53 of apparatus 155, showing a variation wherein the WT material 54n is coupled to the lower surface of the material comprising the WT filter 53.

FIG. 5D is an expanded cross sectional view of a portion of the flexible WT filter 53 of apparatus 155, showing a variation where the WT material 54n is coupled to the upper surface of the material comprising the WT filter 53.

FIG. 5E is an expanded cross sectional view of a portion of the flexible WT filter 53 of apparatus 155, showing a variation where the WT material 54n is laminated between two supporting upper and lower surfaces of the material comprising the WT filter 53.

FIG. 5F is an expanded cross sectional view of a portion of the flexible WT filter 53 of apparatus 155, showing a variation where the WT material 54n is coupled (to support uniform, lower or upper WT material and support material) to wire like shapes that form a mat comprising the material of the WT filter 53.

FIG. 5G is an expanded cross sectional view of a portion of the flexible WT filter 53 of apparatus 155, showing a variation where the WT material is coupled with wire like shapes that form a woven mesh (similar to fiberglass cloth or metal screen) comprising the material of the WT filter 53.

FIG. 5H is an expanded cross sectional view along the line G-G of FIG. 5A of a portion of apparatus 155, comprising the primary UV radiation source 12, the flexible WT filter 53 with WT material 54n, and a lens cover 40.

DETAILED DESCRIPTION OF THE INVENTION

For the purposes of this invention, it will be understood that the primary UV radiation source may comprise: a low-pressure mercury vapor tube, a UV light emitting diode array, a UV emitting xenon bulb, a UV emitting eximer bulb or a UV emitting excimer bulb as described below. Where reference is made to such primary UV radiation source it will be understood to mean a source such as described above. Additionally, other UV sources, such as a laser for example, may also be utilized herein to supply primary UV radiation. The WT materials of any preferred embodiments may comprise any material or system that absorbs light of one wavelength or band of wavelengths and emits light of another wavelength or band of wavelengths, thus modifying the distribution of spectral emission. Such materials or systems include band pass filters, phosphors and include also such materials or systems such as quantum dots whose properties are a combination of bulk properties and their physical particle size. Although the WT materials used in similar applications are typically phosphors, any of a wide variety of WT materials (including phosphors) may be used in this invention without departing from the teaching herein. Further, the WT materials may have structural properties such that the material is self supporting, or the WT materials may need to be supported by a structural member If support is needed, the WT materials may be coupled to either side of a UV transmitting support surface, bonded between UV transmitting support surfaces, sandwiched between two layers of UV transmitting materials, or the WT material may be disposed internally to the UV transmitting support material. Further, the WT material may be incorporated into a fiber and then constructed into a mat of fibers (similar to fiber-glass matting) or the material may be woven into a screen (similar to fiber-glass cloth.)

If the WT filter is to be hard and rigid, the material comprising the WT filter can be chosen from the group of materials that includes but is not limited to: natural or synthetic fused quartz or quartz glass, borosilicate glass, natural or synthetic calcium fluoride (also the other metallic fluorides such as barium, lithium, sodium, magnesium, strontium, and lanthanum fluoride), natural or synthetic sapphire, magnesium oxide, hard glass, lime glass, chemical Pyrex, sapphire glass, or UV transmitting or UV minimizing plexiglass. If the WT filter is to be flexible, the material comprising it can be a hard material that is fashioned into a mat or woven into a cloth or mesh that can be flexible, or the material can be chosen from the group of flexible materials that include but are not limited to: silicone polymers and fluoropolymers. One such group of fluoropolymers is the Teflon.RTM family that has acronyms such as ETFE, Tefzel.RTM, PFA, PTFE, FEP and EFEP.

Referring now to the FIGS. 1A through 1E, preferred embodiments of apparatus 150-153 of the present invention, provide a means for selectively producing one or more of a plurality of wavelength distributions of radiation in a hand-held, portable, multi purpose ultraviolet radiation (UV) emitting device.

With reference to FIGS. 1A and 1B, a first preferred embodiment of the present invention, apparatus 150, is shown. The apparatus 150 comprises a housing 10. The housing 10 contains and supports the internal elements as described further below. The housing 10 may be comprised of a variety of materials including plastics, metals, and etcetera as is known to those skilled in the art. The housing 10 further comprises a UV exit port 15 manufactured into the housing 10. As shown, a primary UV radiation source, or lamp, a mercury vapor tube 12 is coupled within the housing 10 positioned such as to allow a primary UV radiation output, and/or a transformed radiation output (see below) to emit radiation via a lens cover 40 that is coupled to the housing 10 integrally filling the exit port 15. The apparatus 150 further comprises a switch 31 coupled within apparatus 150, and protruding through an opening in housing 10.

With reference now to FIG. 1C, a second preferred embodiment of the present invention apparatus 151 is shown. The apparatus 151 comprises a housing 10. The housing 10 contains and supports the internal elements as described further below. The housing 10 may be comprised of a variety of materials including plastics, metals, and etcetera as is known to those skilled in the art. The housing 10 further comprises a UV exit port 15 manufactured into the housing 10. As shown, a primary UV radiation source, a UV LED array 12a is coupled within the housing 10 positioned such as to allow a primary UV radiation output, (and visible light if the LED array is not a pure UV source), and/or a transformed radiation output (discussed further below) to emit radiation via a lens cover 40 that is coupled to the housing 10 integrally filling the exit port 15. The apparatus 151 further comprises a switch 31 coupled within apparatus 151, and protruding through an opening in the housing 10.

With reference now to FIG. 1D, a third preferred embodiment of the present invention apparatus 152 is shown. The apparatus 152 comprises a housing 10. The housing 10 contains and supports the internal elements as described further below. The housing 10 may be comprised of a variety of materials including plastics, composites, metals, and etcetera as is known to those skilled in the art. The housing 10 further comprises a UV exit port 15 manufactured into the housing 10. As shown, a primary UV radiation source, a pair of UV emitting xenon type bulbs 12b is coupled within the housing 10 positioned such as to allow a primary UV radiation output (and visible light if the LED array is not a pure UV source), and/or a transformed radiation output (discussed below) to emit radiation via a lens cover 40 that is coupled to the housing 10 integrally filling the exit port 15. As is well known to those skilled in With reference now to FIG. 1E, a fourth preferred embodiment of the present invention apparatus 153 is shown. The apparatus 153 comprises a housing 10. The housing 10 contains and supports the internal elements as described further below. The housing 10 may be comprised of a variety of materials including plastics, composites, metals, and etcetera as is known to those skilled in the art. The housing 10 further comprises a UV exit port 15 manufactured into the housing 10. As shown, a primary UV radiation source, a pair of UV emitting eximer/excimer type bulbs 12c is coupled within the housing 10 positioned such as to allow a primary UV radiation output, and/or a transformed radiation output as described below to emit radiation via a lens cover 40 that is coupled to the housing 10 integrally filling the exit port 15. As is well known to those skilled in the art, fewer than two and more than two eximer/excimer type bulbs 12c may be utilized in preferred embodiments of the present invention, and the pair shown herein is representative of at least one eximer/excimer type bulb 12c. The apparatus 153 further comprises a switch 31 coupled within apparatus 153, and protruding through an opening in housing 10.

With reference now to FIG. 1A G-G, a cross section of the first preferred embodiment shown in FIG. 1A taken on the line G-G is shown. The apparatus 150 comprises a primary UV radiation source, a low-pressure mercury vapor tube 12 internally coupled to the housing 10. Coupled to the housing 10, is a reflector 19, positioned so as to reflect the primary UV radiation 17 produced by the primary UV radiation source, a low-pressure mercury vapor tube 12 herein, in a preferred direction 20 towards and through the exit port 15 and through the lens cover 40 which integrally occupies the area of the exit port 15, being further coupled to the housing 10. Juxtaposed relative to the lens cover 40, and disposed between the lens cover 40 and the primary UV radiation source, a low-pressure mercury vapor tube 12 herein, is a slideably removable WT filter 23 also comprising WT material 24n. Note that the other enumerated primary UV radiation sources discussed herein may be used rather than the low-pressure mercury vapor tube 12.

With reference to FIGS. 2B-2G, a series of expanded cross-sectional views of the WT filter 23 are shown. Each of these figures depicts one of the preferred systems of integrating the WT filter 23 with the WT material 24n. Each of these WT filters 23 comprises the properties to enable proper system operation in each of the preferred embodiments 150-153 of the present invention.

With reference to FIG. 2B, an expanded cross sectional view of a flexible WT filter 23 of apparatus 150-153, wherein a WT material 24n is uniformly distributed throughout the material comprising the WT filter 23 is shown.

With reference to FIG. 2C, an expanded cross sectional view of a portion of the flexible WT filter 23 of apparatus 150-153, showing a variation wherein the WT material 24n is coupled to the lower surface of the material comprising the WT filter 23 is shown.

With reference to FIG. 2D, an expanded cross sectional view of a portion of the flexible WT filter 23 of apparatus 150-153, showing a variation where the WT material 24n is coupled to the upper surface of the material comprising the WT filter 23 is shown.

With reference to FIG. 2E, an expanded cross sectional view of a portion of the flexible WT filter 23 of apparatus 150-153, showing a variation where the WT material 24n is laminated between two supporting material comprising the upper and lower surfaces of the WT filter 23 is shown.

With reference to FIG. 2F, an expanded cross sectional view of a portion of the flexible WT filter 23 of apparatus 150-153, showing a variation where the WT material 24n is coupled (to support uniform, lower or upper WT material and support material) to wire like shapes that form a mat comprising the material of the WT filter 23 is shown.

With reference to FIG. 2G, an expanded cross sectional view of a portion of the flexible WT filter 23 of apparatus 150-153, showing a variation where the WT material 24n is coupled with wire like shapes that form a woven mesh (similar to fiberglass cloth or metal screen) comprising the material of the WT filter 23 is shown.

Referring to FIG. 2H a blown up view of a portion of the low-pressure mercury vapor tube 12, a portion of the WT filter 23 and a portion of the lens cover 40 is shown. The low-pressure mercury vapor tube 12 emits the primary UV radiation 17 in a preferred direction 20. The WT filter 23, including its WT material 24n, transforms the primary UV radiation 17 into a secondary UV radiation that is different from the primary UV radiation 17. In this figure, the secondary UV radiation is represented by the transformed radiation 18n. The transformed radiation 18n is representative of a range of different secondary UV radiations comprising transformed radiation 18a, 18b, 18c . . . 18n.

With reference to FIG. 2A, an exploded view of the first preferred embodiment of the invention of FIG. 1A showing apparatus 150 incorporating a primary UV radiation source, a low-pressure mercury vapor tube 12 in this preferred embodiment, is shown. The housing 10 is comprised of a housing top 10a, that is coupled to a housing lower bottom half 10b, and wherein both the housing top 10a and the housing lower bottom half 10b are further coupled to housing upper bottom half 10c. The aforementioned housing pieces comprise the housing 10 in preferred embodiments of the present invention discussed herein. The housing 10 serves to support and protect the lower components coupled within the housing 10. Positioned and supported within the bottom end of the housing 10, is a source activation and control assembly 32. Coupled to the source activation and control assembly 32 is the switch 31. The switch 31, a rocker switch in a preferred embodiment of the present invention shown herein, is operated to signal the source activation and control assembly 32 to start and operate the primary UV radiation source. Those skilled in the art will recognize that other types of switches could be used in other preferred embodiments of the present invention. The source activation and control assembly 32 contains electrical circuitry to start and operate the primary UV radiation source, a low-pressure mercury vapor tube 12 in a preferred embodiment of the present invention. As will be understood by those well versed in the art, the source activation and control assembly 32 in other preferred embodiments comprises the electrical circuitry to start and operate the UV LED array 12a, UV emitting xenon type bulbs 12b, UV emitting eximer/excimer type bulbs 12c, that are shown in the accompanying figures, and which may be used as the primary UV source herein. Additionally, other UV emitting sources known to those skilled in the art may also be utilized herein. Coupled to the source activation and control assembly 32 is a pair of batteries 30. The batteries 30 provide electrical power via the source activation and control assembly 32 to the primary UV radiation source, a low-pressure mercury vapor tube 12 in a preferred embodiment of the present invention. It will be understood by those skilled in the art that a single battery may be used in some preferred embodiments of the present invention.

With reference now to FIG. 2I, an external power supply assembly 45 is shown. The power adapter assembly 45 comprises a power source 46 coupled via a connecting electrical cable 49 to a low voltage power coupling 47. The low voltage power coupling 47 couples to the activation and control assembly 32 via a power input jack, not shown herein, in a manner well known to those skilled in the art. The external power supply assembly 45 provides electrical power to charge the batteries 30 wherein such batteries are re-chargeable. Additionally, the external power supply assembly 45, in preferred embodiments of the present invention may further provide operating power to start and operate a primary UV radiation source in preferred embodiments of the present invention while re-charging the batteries 30.

With reference back to FIG. 2A, a lens cover 40 is shown. The lens cover 40 may be either clearly transparent in a first mode of operation, or in a second mode of operation, the lens cover may be a transparent purple. The lens cover 40 is coupled to the housing top 10a, which is integral to the housing 10. The lens cover 40 integrally fills the exit port 15. Further coupled to the housing 10, is a reflector 19, positioned so as to reflect the primary UV radiation 17 produced by the primary UV radiation source, a low-pressure mercury vapor tube 12 herein, in a preferred direction 20 towards and through the exit port 15 and through the lens cover 40. The lens cover 40 will pass the primary UV radiation 17 and, the transformed radiation 18n in the preferred direction 20.

The apparatus 150 further comprises a primary UV radiation source, a low-pressure mercury vapor tube 12 internally coupled to the housing 10. It should be noted that the noted primary UV radiation sources discussed herein, apparatus 150-153, may also be coupled in place rather than the low-pressure mercury vapor tube 12. Juxtaposed relative to the lens cover 40, and between the lens cover 40 and the primary UV radiation source, a low-pressure mercury vapor tube 12 herein, is the slideably removable WT filter 23. The WT filter 23 may be slid laterally into a WT filter insertion slot 60, in such a manner as to place one or more of the WT materials 24a, 24b, 24c . . . 24n, (only 24n is shown in the figures) between the primary UV radiation source 12 and the radiation exit port 15 thus causing untransformed primary radiation 17 or transformed radiations 18, 18a, 18b, 18c, 18n, (only 18n is shown in the figures), to be emitted from the apparatus 150. It should be noted that the above description is also applicable to apparatus 151-153 discussed above as well as apparatus 154-156 discussed below.

With reference now to FIG. 3A, a rotatable substantially flat disk WT filter 33 with WT material 34n is shown. The WT filer 33 is used in combination with a fifth preferred embodiment of the invention, shown in FIG. 3H, apparatus 156. Portions of the substantially flat disk shaped WT filter 33 are coupled with different WT materials 34n, each of which is capable of producing a transformed radiation 18n upon irradiation by the primary UV radiation 17.

With reference to FIG. 3H, a plan view of the fifth preferred embodiment of the invention, apparatus 156, comprising the rotatable disk shaped WT filter 33 of FIG. 3A is shown. In this preferred embodiment, the rotatable disk shaped WT filter 33 is inserted into and juxtaposed between a primary UV radiation source 17, a UV LED array 12a is shown herein although any of the primary UV radiation sources 12-12c could be utilized herein, and the UV exit port 15. The housing 10 has been modified in this preferred embodiment, apparatus 156, such that the UV exit port 15, manufactured into the housing 10, is pie-shaped, thus blocking any radiation, primary or transformed, from being emitted without first passing through the rotatable disk shaped WT filter 33. The modifications to the housing 10 and the exit port 15 enables the rotatable disk shaped WT filter 33 to be rotated, see directional arrow 36, such that a desired segment of the rotatable disk shaped WT filter 33 may be positioned to enable a particular segment of WT filter 33 comprising a desired WT material 34n to substantially fill the opening of the exit port 15, thus allowing a primary UV radiation 17 output, and/or a transformed radiation 18n output (see above) to be emitted via the lens cover 40 that is coupled to the housing 10 integrally filling the exit port 15. The apparatus 156 further comprises a switch 31 coupled within apparatus 156, and protruding through an opening in the housing 10.

Additionally, in this fifth preferred embodiment of the invention, apparatus 156, a portion of the substantially flat disk shaped WT filter 33 can remain transparent to the primary UV radiation 17, or even have a portion of the substantially flat disk shaped WT filter 33 missing. To easily switch between different radiation emissions, transformed or untransformed, the substantially flat disk shaped WT filter 33 is rotated such that the desired WT material 34n, a transparent region, or a void or slit in the flat filter, or a combination thereof, lies between the primary UV radiation 17, or the transformed radiation 18n, and the exit port 15 of the apparatus 156.

With reference to FIGS. 3B-3G, a series of expanded cross-sectional views of the WT filter 33, taken along plane s-s-s of FIG. 3a, are shown. Each of these figures depicts one of the preferred systems of integrating the WT filter 33 with the WT material 34n. Each of these WT filter sections 33 comprises the properties to enable proper system operation of the preferred embodiment, apparatus 156, of the present invention.

With reference to FIG. 3B, an expanded cross sectional view of a flexible WT filter 33 of apparatus 156, wherein a WT material 34n is uniformly distributed throughout the material comprising the WT filter 33 is shown.

With reference to FIG. 3C, an expanded cross sectional view of a portion of the flexible WT filter 33 of apparatus 156, showing a variation wherein the WT material 34n is coupled to the lower surface of the material comprising the WT filter 33 is shown.

With reference to FIG. 3D, an expanded cross sectional view of a portion of the flexible WT filter 33 of apparatus 156, showing a variation where the WT material 34n is coupled to the upper surface of the material comprising the WT filter 33 is shown.

With reference to FIG. 3E, an expanded cross sectional view of a portion of the flexible WT filter 33 of apparatus 156, showing a variation where the WT material 34n is laminated between two supporting material comprising the upper and lower surfaces of the WT filter 33 is shown.

With reference to FIG. 3F, an expanded cross sectional view of a portion of the flexible WT filter 33 of apparatus 156, showing a variation where the WT material 34n is coupled (to support uniform, lower or upper WT material and support material) to wire like shapes that form a mat comprising the material of the WT filter 33 is shown.

With reference to FIG. 3G, an expanded cross sectional view of a portion of the flexible WT filter 33 of apparatus 156, showing a variation where the WT material 34n is coupled with wire like shapes that form a woven mesh (similar to fiberglass cloth or metal screen) comprising the material of the WT filter 33 is shown.

With reference now to FIG. 4A G-G, a cross section of the sixth preferred embodiment shown in FIG. 1A taken on the line G-G is shown. The apparatus 154 comprises a primary UV radiation source, a low-pressure mercury vapor tube 12 internally coupled to the housing 10. Coupled to the housing 10, is a reflector 19, positioned so as to reflect the primary UV radiation 17 produced by the primary UV radiation source, a low-pressure mercury vapor tube 12 herein, in a preferred direction 20 towards and through the exit port 15 and through the lens cover 40 which integrally occupies the area of the exit port 15, being further coupled to the housing 10. Juxtaposed relative to the lens cover 40, and disposed between the lens cover 40 and the primary UV radiation source, a low-pressure mercury vapor tube 12 herein, is a WT filter 43 in the form of a flexible belt comprising UV transmitting material that is coupled to WT materials 44n. The WT filter 43 is rolled around a pair of rollers 59 that are coupled to the housing 10. The WT filter 43 may be moved back and forth with the WT filter 43 flexible belt material being rolled upon the rollers 59. The rollers 59 may be rotated, arrows 56, clockwise or counter-clockwise which will enable the desired portions the WT materials 44n to become Juxtaposed relative to the lens cover 40, and disposed between the lens cover 40 and the primary UV radiation source, a low-pressure mercury vapor tube 12 herein. As previously discussed, although this figure comprises a low-pressure mercury vapor tube 12, the UV LED array 12a, UV emitting xenon type bulbs 12b, and UV emitting eximer/excimer type bulbs 12c, that are shown in the accompanying FIGS., may be used as the primary UV source herein juxtaposed between the WT filter 43 flexible belt material, and the reflector 19.

With reference to FIGS. 4B-4G, a series of expanded cross-sectional views of the WT filter 43 are shown. Each of these figures depicts one of the preferred systems of integrating the WT filter 43 with the WT material 44n in a manner comprising the flexible belt. Each of these WT filters 43 comprises the properties to enable proper system operation of the preferred embodiment, apparatus 155, of the present invention.

With reference to FIG. 4B, an expanded cross sectional view of a flexible WT filter 43 of apparatus 154, wherein a WT material 44n is uniformly distributed throughout the material comprising the WT filter 43 is shown.

With reference to FIG. 4C, an expanded cross sectional view of a portion of the flexible WT filter 43 of apparatus 154, showing a variation wherein the WT material 44n is coupled to the lower surface of the material comprising the WT filter 43 is shown.

With reference to FIG. 4D, an expanded cross sectional view of a portion of the flexible WT filter 43 of apparatus 154, showing a variation where the WT material 44n is coupled to the upper surface of the material comprising the WT filter 43 is shown.

With reference to FIG. 4E, an expanded cross sectional view of a portion of the flexible WT filter 43 of apparatus 154, showing a variation where the WT material 44n is laminated between two supporting material comprising the upper and lower surfaces of the WT filter 43 is shown.

With reference to FIG. 4F, an expanded cross sectional view of a portion of the flexible WT filter 43 of apparatus 154, showing a variation where the WT material 44n is coupled (to support uniform, lower or upper WT material and support material) to wire like shapes that form a mat comprising the material of the WT filter 43 is shown.

With reference to FIG. 4G, an expanded cross sectional view of a portion of the flexible WT filter 43 of apparatus 154, showing a variation where the WT material 44n is coupled with wire like shapes that form a woven mesh (similar to fiberglass cloth or metal screen) comprising the material of the WT filter 43 is shown.

Referring to FIG. 4H a blown up view of a portion of the low-pressure mercury vapor tube 12, a portion of the WT filter 43 and a portion of the lens cover 40 is shown. The low-pressure mercury vapor tube 12 emits the primary UV radiation 17 in a preferred direction 20. The WT filter 43, including its WT material 44n, transforms the primary UV radiation 17 into a secondary UV radiation that is different from the primary UV radiation 17. In this figure, the secondary UV radiation is represented by the transformed radiation 18n. The transformed radiation 18n is representative of a range of different secondary UV radiations comprising transformed radiation 18a, 18b, 18c . . . 18n.

With reference now to FIG. 5A G-G, a cross section of the sixth preferred embodiment shown in FIG. 1A taken on the line G-G is shown. The apparatus 155 comprises a primary UV radiation source, a low-pressure mercury vapor tube 12 internally coupled to the housing 10. Coupled to the housing 10, is a reflector 19, positioned so as to reflect the primary UV radiation 17 produced by the primary UV radiation source, a low-pressure mercury vapor tube 12 herein, in a preferred direction 20 towards and through the exit port 15 and through the lens cover 40 which integrally occupies the area of the exit port 15, being further coupled to the housing 10. Juxtaposed relative to the lens cover 40, and disposed between the lens cover 40 and the primary UV radiation source, a low-pressure mercury vapor tube 12 herein, is a WT filter 53 in the form of a continuous flexible belt comprising UV transmitting material that is coupled to WT materials 54n. The WT filter 53 is placed around, and supported by, a pair of rollers 59 that are coupled to the housing 10. The WT filter 53 may be moved back and forth with the WT filter 53 continuous flexible belt material being rolled past the rollers 59. The rollers 59 may be rotated, arrows 56, clockwise or counter-clockwise which will enable the desired portions the WT materials 54n to become Juxtaposed relative to the lens cover 40, and disposed between the lens cover 40 and the primary UV radiation source, a low-pressure mercury vapor tube 12 herein. As previously discussed, although this figure comprises a low-pressure mercury vapor tube 12, the UV LED array 12a, UV emitting xenon type bulbs 12b, and UV emitting eximer/excimer type bulbs 12c, that are shown in the accompanying FIGS., may be used as the primary UV source herein juxtaposed between the WT filter 53 continuous flexible belt material, and the reflector 19.

With reference to FIGS. 5B-5G, a series of expanded cross-sectional views of the WT filter 53 are shown. Each of these figures depicts one of the preferred systems of integrating the WT filter 53 with the WT material 54n in a manner comprising the continuous flexible belt. Each of these WT filters 53 comprises the properties to enable proper system operation of the preferred embodiments, apparatus 155, of the present invention.

With reference to FIG. 5B, an expanded cross sectional view of a continuous flexible WT filter 53 of apparatus 155, wherein a WT material 54n is uniformly distributed throughout the material comprising the WT filter 53 is shown.

With reference to FIG. 5C, an expanded cross sectional view of a portion of the continuous flexible WT filter 53 of apparatus 155, showing a variation wherein the WT material 54n is coupled to the lower surface of the material comprising the WT filter 53 is shown.

With reference to FIG. 5D, an expanded cross sectional view of a portion of the continuous flexible WT filter 53 of apparatus 155, showing a variation where the WT material 54n is coupled to the upper surface of the material comprising the WT filter 53 is shown.

With reference to FIG. 5E, an expanded cross sectional view of a portion of the continuous flexible WT filter 53 of apparatus 155, showing a variation where the WT material 54*n* is laminated between two supporting material comprising the upper and lower surfaces of the WT filter 53 is shown.

With reference to FIG. 5F, an expanded cross sectional view of a portion of the continuous flexible WT filter 53 of apparatus 155, showing a variation where the WT material 54*n* is coupled (to support uniform, lower or upper WT material and support material) to wire like shapes that form a mat comprising the material of the WT filter 53 is shown.

With reference to FIG. 5G, an expanded cross sectional view of a portion of the continuous flexible WT filter 53 of apparatus 155, showing a variation where the WT material 54*n* is coupled with wire like shapes that form a woven mesh (similar to fiberglass cloth or metal screen) comprising the material of the WT filter 53 is shown.

Referring to FIG. 5H a blown up view of a portion of the low-pressure mercury vapor tube 12, a portion of the WT filter 53 and a portion of the lens cover 40 is shown. The low-pressure mercury vapor tube 12 emits the primary UV radiation 17 in a preferred direction 20. The WT filter 53, including its WT material 54*n*, transforms the primary UV radiation 17 into a secondary UV radiation that is different from the primary UV radiation 17. In this figure, the secondary UV radiation is represented by the transformed radiation 18*n*. The transformed radiation 18*n* is representative of a range of different secondary UV radiations comprising transformed radiation 18*a*, 18*b*, 18*c* . . . 18*n*.

Operation

With reference to all of the FIGS., the preferred embodiments of the present invention, apparatus 150-156, a hand-held portable multi purpose sterilizing wavelength transforming converter, are operated as follows to emit UV ultraviolet radiation (UV) and visible light. Following activation of the switch 31, the source activation and control assembly 32 supplies power to the primary UV radiation source: a low-pressure mercury vapor tube 12, a UV LED array 12*a*, a UV emitting xenon type bulb 12*b*, or a UV emitting eximer/excimer type bulb 12*c*. The primary UV radiation source emits primary UV radiation 17 in a preferred direction 20.

In a first mode of operation, if the primary UV source is pure i.e. the source emits little, if any, visible light, the primary UV radiation 17 is all, or substantially all UV C. A transparent lens cover 40 will pass the primary UV radiation 17. The effect of the apparatus 150-156 emission of UV C will be to cause the sterilization of surfaces, air, or liquids after the UV C is directed for a sufficient period of time towards the material to be sterilized. UV C at a wavelength of approximately 254 nm kills germs, fungus, bacteria, viruses, molds, and etcetera by breaking bonds in the DNA (see www.fluorescents.com for a good discussion of this process on the FAQ page. In this mode, it does not matter if the primary UV C radiation source also produces some visible light because the visible light does not interfere with the sterilization process.

It should be also be noted that the mercury vapor bulbs/tubes do emit visible light, i.e. they are not pure generally, and emit both UV C and some visible light. Conversely, some LED's and the excimer/eximer lamps can emit clean UV C, although depending on the desires on the user, LEDs and excimer/eximer lamps may also emit visible light.

If another combination of UV radiation is desired, for example UV B, then the desired WT filter and associated WT transforming material 23/24*n*, 33/34*n*, 43/44*n*, 53/54*n*, is placed in the path of the primary UV radiation 17. This is accomplished as previously discussed by inserting the WT filter 23 into the WT filter insertion slot 60 (apparatus 150-153); rotating the rotatable disk shaped WT filter 33 (apparatus 156); or by positioning the WT filter 43 or 53. This insertion would transform the primary UV radiation 17 into a transformed radiation 18*n*. The conversion to UC B provides an additional feature for the preferred embodiments 150-156 of the present invention, as UV B of approximately 280 nm (at the low end of the UV B spectra), makes certain proteins fluoresce and in the process, the UV B damages the protein thus providing another means of sterilization.

Under some conditions, an apparatus that emits a combination of both 254 nm UV C and 280 nm UV B would be more effective at sterilizing than one which only emits one of those wavelengths or the other wavelength. Therefore, by selecting yet another desired WT filter and associated WT transforming material 23/24*n*, 33/34*n*, 43/44*n*, 53/54*n*, to be placed in the path of the primary UV radiation 17, the preferred embodiments 150-156 of the present invention would simultaneously provide two ways to damage the fungus, mold, and etcetera rather than just one way. The WT filter and associated WT transforming material 23/24*n*, 33/34*n*, 43/44*n*, 53/54*n* can be made such by the user that only a desired percentage of the 254 nm primary radiation 17 UV C will be transformed into 280 nm UV transformed radiation 18*n*. The ratio of 254 nm UV to 280 nm UV may be varied as desired by adjusting the amount of the WT transforming material 24*n*, 34*n*, 44*n*, 54*n* in the WT filter 23, 33, 43, 53. It should be noted that this may be embodied, as previously discussed, by making a plurality of WT filters filter 23, 33, 43, 53 each having its own unique WT transforming materials 24*n*, 34*n*, 44*n*, 54*n* thus enabling the plurality of transformed radiations 18, 18*a*, 18*b*, 18*c*, 18*n*.

Additionally, if the primary UV source is pure, or substantially pure, the primary UV radiation 17 of these preferred embodiments of the present invention, apparatus 150-156, can also be used for making materials fluoresce because the apparatus 150-156 emits UV C radiation, primary radiation 17, and the selection of desired WT filter and associated WT transforming material 23/24*n*, 33/34*n*, 43/44*n*, 53/54*n*, to be placed in the path of the primary UV radiation 17, will further enable the preferred embodiments 150-156 of the present invention to selectively emit transformed radiation 18*a*, 18*b*, 18*c*, . . . 18*n* which will produce UV B, UV A or any band or blend of UV radiation.

Lastly, if the primary UV source is pure, the primary UV radiation 17 of these preferred embodiments of the present invention, apparatus 150-156, can also be used for making visible, or substantially visible, light because the apparatus 150-156 emits UV C radiation, primary radiation 17, and the selection of desired WT filter and associated WT transforming material 23/24*n*, 33/34*n*, 43/44*n*, 53/54*n*, be placed in the path of the primary UV radiation 17, will cause a transformed radiation 18*n* in the form of visible light to be developed and emitted. This provides another important feature of the preferred embodiments of the present invention, apparatus 150-156, the functioning as a visible light or torch, in addition to the emission of UV C, UV A, UV B, UV A+B, as transformed radiation 18*n*.

In a second mode of operation, if the primary UV source is not pure, i.e. the source emits visible light, then the primary UV radiation 17 is not all, or substantially all UV C. In this case, a transparent lens cover 40 will pass the primary UV radiation 17 and the visible light at the same time. The effect of the apparatus 150-156 emission of UV C will be to cause the sterilization of surfaces, air, or liquids after the UV C is directed for a sufficient period of time towards the material to be sterilized, while providing visible light for a torch at the same time. As previously discussed, the UV C at a wavelength of approximately 254 nm kills germs, fungus, bacteria, viruses, molds, and etcetera by breaking bonds in the DNA.

As was previously discussed, it should be noted that the mercury vapor bulbs/tubes do emit visible light, i.e. they are not pure generally, and emit both UV C and some visible light. And conversely, while some LED's and the excimer/eximer lamps can emit clean UV C, some may be selected to purposely emit visible light.

If another combination of UV radiation is desired, for example UV B, then the desired WT filter and associated WT transforming material 23/24n, 33/34n, 43/44n, 53/54n, is placed in the path of the primary UV radiation 17. This is accomplished as previously discussed by inserting the WT filter 23 into the WT filter insertion slot 60 (apparatus 150-153); rotating the rotatable disk shaped WT filter 33 (apparatus 156); or by positioning the WT filter 43 or 53. This insertion would transform the primary UV radiation 17 into a transformed radiation 18n. The conversion to UC B provides an additional feature for the preferred embodiments 150-156 of the present invention, as UV B of approximately 280 nm (at the low end of the UV B spectra), makes certain proteins fluoresce and in the process, the UV B damages the protein thus providing another means of sterilization, while also providing visible light for a torch at the same time.

Under some conditions, a UV lamp fixture that emits a combination of BOTH 254 nm UV C AND 280 nm UV B would be more effective at sterilizing that one which only emits one of those wavelengths or the other wavelength. Therefore, by selecting yet another desired WT filter and associated WT transforming material 23/24n, 33/34n, 43/44n, 53/54n, to be placed in the path of the primary UV radiation 17, the preferred embodiments 150-156 of the present invention would simultaneously provide two ways to damage the fungus, mold, and etcetera rather than just one way. The WT filter and associated WT transforming material 23/24n, 33/34n, 43/44n, 53/54n can be made such by the user that only a desired percentage of the 254 nm primary radiation 17 UV C will be transformed into 280 nm UV transformed radiation 18n. The ratio of 254 nm UV to 280 nm UV may be varied as desired by adjusting the amount of the WT transforming material 24n, 34n, 44n, 54n in the WT filter 23, 33, 43, 53. It should be noted that this may be embodied, as previously discussed, by making a plurality of WT filters filter 23, 33, 43, 53 each having its own unique WT transforming materials 24n, 34n, 44n, 54n thus enabling the plurality of transformed radiations 18, 18a, 18b, 18c, 18n, while providing visible light for a torch at the same time.

As previously discussed, in the first mode of operation, if the primary UV source is pure, or substantially pure, the primary UV radiation 17 of these preferred embodiments of the present invention, apparatus 150-156, can also be used for making materials fluoresce. In the second mode of operation however, because the primary radiation 17 also comprises visible light, this would substantially prevent the fluorescent effect from being seen. Therefore, if fluorescing is desired, a purple colored transparent lens cover 40 may be used in place of the clear transparent lens cover 40. The purple colored transparent lens cover 40 will filter out the visible light component of the primary UV radiation 17 thus enabling the fluorescent effect. i.e. the purple color transparent lens cover 40 acts as a visible light blocking—UV transmitting band pass filter.

Additionally, with either the clear, or the purple color transparent lens cover 40 in place coupled to the housing 10 integrally filling the exit port 15, the apparatus 150-156 will emit UV C radiation, primary radiation 17; and the user may select desired WT filter and associated WT transforming material 23/24n, 33/34n, 43/44n, 53/54n, to be placed in the path of the primary UV radiation 17, which will further enable the preferred embodiments 150-156 of the present invention to selectively emit transformed radiation 18a, 18b, 18c, ... 18n which will produce UV B, UV A or any band or blend of UV radiation. The presence of the clear or the purple colored transparent lens cover 40 will control whether visible light is also emitted thus providing a visible light torch function at the same time as the primary UV radiation and/or the transformed radiation 18n.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. It will doubtless be understood to those of ordinary skill in the art that there are other embodiments employing these principles that are not described in detail herein.

I claim:

1. A portable handheld sterilizer and torch apparatus for producing multiple and variable wavelength distributions of UV or visible radiation, comprising:
   a handheld portable case, having an exit port;
   a primary ultraviolet radiation source disposed within said handheld portable case wherein said ultraviolet radiation source produces a primary wavelength distribution;
   a source activation and control assembly coupled to said ultraviolet radiation source;
   a lens cover coupled to an upper side of said handheld portable case;
   at least one battery coupled to said source activation and control assembly; and
   at least one wavelength-transforming filter, positionable during use between said primary ultraviolet radiation source and the exit port, wherein said at least one wavelength-transforming filter in response to irradiation by said primary ultraviolet radiation source, emits a secondary UV or visible radiation.

2. The apparatus of claim 1 wherein said lens cover is transparent.

3. The apparatus of claim 2 wherein said secondary UV or visible radiation comprises a spread of energy distribution with a large portion of the energy at approximately 254 nm UV C.

4. The apparatus of claim 3 wherein said secondary UV or visible radiation comprises a spread of energy distribution with a large portion of the energy at approximately 280 nm UV B 5. The apparatus of claim 2 wherein said secondary UV or visible radiation comprises a spread of energy distribution with a large portion of the energy at approximately 280 nm UV B.

6. The apparatus of claim 5 wherein said secondary UV or visible radiation comprises a spread of energy distribution with a large portion of the energy at approximately 254 nm UV C.

7. The apparatus of claim 1 wherein said lens cover is a band pass filter.

8. The apparatus of claim 7 wherein said secondary UV or visible radiation comprises a spread of energy distribution with a large portion of the energy at approximately 254 nm UV C and at approximately 280 nm UV B.

9. A portable handheld sterilizer and torch apparatus for producing multiple and variable wavelength distributions of UV or visible radiation, comprising:
   a handheld portable case, having an exit port;

a primary ultraviolet radiation source disposed within said handheld portable case wherein said ultraviolet radiation source produces a primary substantially pure UV wavelength distribution;

a source activation and control assembly coupled to said ultraviolet radiation source;

a lens cover coupled to an upper side of said handheld portable case;

at least one battery coupled to said source activation and control assembly; and at least one wavelength-transforming filter, positionable during use between said primary ultraviolet radiation source and the exit port, wherein said at least one wavelength-transforming filter in response to irradiation by said primary ultraviolet radiation source, emits a secondary UV or visible radiation.

10. The apparatus of claim 9 wherein said lens cover is transparent.

11. The apparatus of claim 10 wherein said secondary UV radiation comprises a spread of energy distribution with a large portion of the energy at approximately 254 nm UV C and at approximately 280 nm UV B.

12. The apparatus of claim 9 wherein said wavelength transforming filter transforms said primary UV wavelength distribution to a visible wavelength distribution.

13. A portable handheld sterilizer and torch apparatus for producing multiple and variable wavelength distributions of UV or visible radiation, comprising:

a handheld portable case, having an exit port;

a primary ultraviolet radiation source disposed within said handheld portable case wherein said ultraviolet radiation source produces a primary wavelength distribution comprising substantially visible radiation;

a source activation and control assembly coupled to said ultraviolet radiation source;

a lens cover coupled to an upper side of said handheld portable case;

at least one battery coupled to said source activation and control assembly; and at least one wavelength-transforming filter, positionable during use between said primary ultraviolet radiation source and the exit port, wherein said at least one wavelength-transforming filter in response to irradiation by said primary ultraviolet radiation source, emits a secondary UV or visible radiation.

14. The apparatus of claim 13 wherein said lens cover is a band pass filter.

15. The apparatus of claim 14 wherein said secondary UV radiation comprises a spread of energy distribution with a large portion of the energy at approximately 254 nm UV C and at approximately 280 nm UV B.

16. The apparatus of claim 13 wherein said lens cover is transparent.

17. The apparatus of claim 16 wherein said secondary UV radiation comprises a spread of energy distribution with a large portion of the energy at approximately 254 nm UV C and at approximately 280 nm UV B.

* * * * *